United States Patent
Brown et al.

(10) Patent No.: US 7,858,649 B2
(45) Date of Patent: Dec. 28, 2010

(54) IMIDAZOLE DERIVATIVES AND THEIR USE FOR MODULATING THE GABA$_A$ RECEPTOR COMPLEX

(75) Inventors: William Dalby Brown, Søborg (DK); Janus S. Larsen, Holbæk (DK); Lene Teuber, Værløse (DK); David Tristram Brown, Albertslund (DK); Philip K. Ahring, Bagsværd (DK); Naheed Mirza, Birkerød (DK); Elsebet Østergaard Nielsen, København K (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/083,352

(22) PCT Filed: Oct. 12, 2006

(86) PCT No.: PCT/EP2006/067313

§ 371 (c)(1),
(2), (4) Date: Aug. 8, 2008

(87) PCT Pub. No.: WO2007/042544

PCT Pub. Date: Apr. 19, 2007

(65) Prior Publication Data

US 2009/0163566 A1 Jun. 25, 2009

Related U.S. Application Data

(60) Provisional application No. 60/726,679, filed on Oct. 17, 2005.

(30) Foreign Application Priority Data

Oct. 14, 2005 (DK) ................................ 2005 01443

(51) Int. Cl.
C07D 413/14 (2006.01)
C07D 413/04 (2006.01)
A61K 31/4245 (2006.01)
A61K 31/4439 (2006.01)

(52) U.S. Cl. .................... 514/364; 548/131; 546/269.1; 514/330

(58) Field of Classification Search ............. 548/311.1, 548/312.4, 314.7, 315.1, 315.4
See application file for complete search history.

(56) References Cited

U.S. PATENT DOCUMENTS

| 4,952,698 A | * | 8/1990 | Biere et al. ................. 548/131 |
| 5,179,111 A | | 1/1993 | Biere et al. |
| 2003/0055085 A1 | * | 3/2003 | Wagenen et al. ............ 514/333 |
| 2006/0217420 A1 | * | 9/2006 | Cosford et al. ............. 514/332 |

FOREIGN PATENT DOCUMENTS

| DE | WO 8801268 A | * | 2/1988 |
| EP | 0 323 799 A1 | | 7/1989 |
| WO | WO-88/01268 A1 | | 2/1988 |
| WO | WO-00/78728 A1 | | 12/2000 |
| WO | WO-02/068417 A2 | | 9/2002 |
| WO | WO-03/053922 A2 | | 7/2003 |

* cited by examiner

*Primary Examiner*—Rebecca L Anderson
*Assistant Examiner*—Matthew P Coughlin
(74) *Attorney, Agent, or Firm*—Birch, Stewart, Kolasch and Birch, LLP

(57) ABSTRACT

This invention relates to novel imidazole derivatives, pharmaceutical compositions containing these compounds, and methods of treatment therewith. The compounds of the invention are of the general formula (I) and include any of its stereoisomers, any mixture of its stereoisomers, and pharmaceutically acceptable salts thereof. The compounds of the invention are useful in the treatment of central nervous system diseases and disorders, which are responsive to modulation of the GABA$_A$ receptor complex, and in particular for combating anxiety and related diseases.

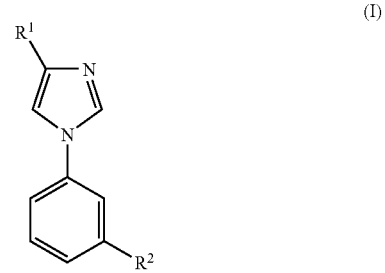

(I)

4 Claims, No Drawings

IMIDAZOLE DERIVATIVES AND THEIR USE FOR MODULATING THE GABA$_A$ RECEPTOR COMPLEX

TECHNICAL FIELD

This invention relates to novel imidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the targets for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha 1$ subunit of the GABA$_A$ receptors. Thus compounds with selectivity for the $\alpha 2$ and/or $\alpha 3$ subunits over the $\alpha 1$ subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

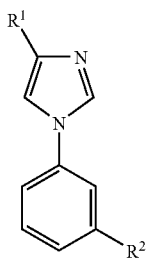

(I)

any of its isomers or any mixture of its isomers, or a pharmaceutically acceptable salt thereof, wherein R$^1$ and R$^2$ are defined as below.

In its second aspect, the invention provides a pharmaceutical composition, comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Imidazole Derivatives

In its first aspect the present invention provides a compound of the general formula (I):

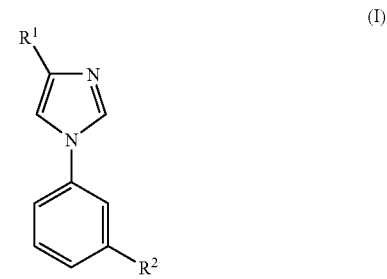

(I)

any of its isomers or any mixture of its isomers, or a pharmaceutically acceptable salt thereof, wherein R$^1$ represents a heterocyclic group;
which heterocyclic group is optionally substituted with one or more substituents independently selected from the group consisting of:
halo, hydroxy, hydroxyalkyl, R$^a$R$^b$N—, R$^a$R$^b$N-alkyl, cyano, nitro, trifluoromethyl, trifluoromethoxy, alkoxy, cycloalkoxy, alkyl, cycloalkyl, cycloalkylalkyl, alkenyl, and alkynyl;
wherein R$^a$ and R$^b$ independent of each other are hydrogen or alkyl;

R$^2$ represents
halo or R$^c$—(C=O)—(NR$^d$)—;
wherein R$^c$ is hydrogen, alkyl; cycloalkyl, cycloalkylalkyl, alkenyl, or alkynyl;
R$^d$ is hydrogen or alkyl; or
an aryl or heteroaryl group;
which aryl or heteroaryl group is optionally substituted with one or more substituents independently selected from the group consisting of:
halo, hydroxy, R$^e$R$^f$N—, R$^e$R$^f$N-alkyl, R$^e$R$^f$N—(C=O)—, cyano, nitro, trifluoromethyl, trifluoromethoxy, alkoxy, cycloalkoxy, R$^e$—(C=O)—, $R^e$—O—(C=O)—, alkyl, cycloalkyl, cycloalkylalkyl, alkenyl, and alkynyl;
wherein $R^e$ and $R^f$ independent of each other are hydrogen or alkyl.

In one embodiment, $R^1$ represents a heterocyclic group; which heterocyclic group is optionally substituted with one or more alkyl.

In a second embodiment, $R^1$ represents an optionally substituted heterocyclic group; which heterocyclic group is selected from the group consisting of:
oxadiazolyl, benzoimidazol, benzooxazolyl, benzothiazolyl, 4,5-dihydro-oxazolyl, furanyl, pyrazolyl and imidazolyl.

In special embodiment, $R^1$ represents optionally substituted [1,2,4]oxadiazolyl, such as 3-methyl-[1,2,4]oxadiazol-5-yl. In a further embodiment, $R^1$ represents optionally substituted [1,3,4]oxadiazolyl, such as 5-methyl-[1,3,4]oxadiazol-3-yl. In a still further embodiment, $R^1$ represents optionally substituted benzimidazolyl, such as 1H-benzimidazol-2-yl. In a further embodiment, $R^1$ represents optionally substituted benzoxazolyl, such as benzooxazol-2-yl. In a still further embodiment, $R^1$ represents optionally substituted benzothiazolyl, such as benzothiazol-2-yl. In a further embodiment, $R^1$ represents optionally substituted 4,5-dihydro-oxazolyl, such as 4,5-dihydro-oxazol-2-yl. In a still further embodiment, $R^1$ represents optionally substituted furanyl, such as 5-methyl-furan-2-yl. In a further embodiment, $R^1$ represents optionally substituted pyrazolyl, such as pyrazol-1-yl. In a still further embodiment, $R^1$ represents optionally substituted imidazolyl, such as imidazol-1-yl.

In a further embodiment, $R^2$ represents halo or $R^c$—(C=O)—(NR$^d$)—; wherein $R^c$ is hydrogen or alkyl; and $R^d$ is hydrogen or alkyl. In a special embodiment $R^2$ represents halo, such as bromo. In a further embodiment, $R^2$ represents $R^c$—(C=O)—(NR$^d$)— wherein $R^c$ is hydrogen or alkyl; and $R^d$ is hydrogen. In a further embodiment, $R^2$ represents acetylamino.

In a still further embodiment, $R^2$ represents an aryl or heteroaryl group; which aryl or heteroaryl group is optionally substituted with one or more substituents independently selected from the group consisting of:
halo, cyano, nitro, trifluoromethyl, trifluoromethoxy, alkoxy, $R^e$—(C=O)—, $R^e$—O—(C=O)— and alkyl wherein $R^e$ and $R^f$ independent of each other are hydrogen or alkyl.

In a special embodiment, $R^2$ represents an optionally substituted phenyl, such as phenyl, halophenyl, such as fluorophenyl, in particular 2-fluoro-phen-1-yl, cyanophenyl, in particular 2-cyano-phen-1-yl, carboxyphenyl, in particular 2-carboxyphen-1-yl, alkoxyphenyl, such as methoxyphenyl or ethoxyphenyl, in particular 2-methoxy-phen-1-yl or 2-ethoxy-phen-1-yl, acetylphenyl, in particular 2-acetylphen-1-yl, alkylphenyl, such as ethylphenyl, in particular 2-ethylphen-1-yl, or trifluoromethoxyphenyl, in particular 2-trifluoromethoxyphen-1-yl, In a further embodiment, $R^2$ represents a disubstituted phenyl, such as dialkoxyphenyl, such as dimethoxyphenyl, in particular 2,5-dimethoxyphen-1-yl, or alkoxy-halophenyl, such as methoxy-fluorophenyl, in particular 5-fluoro-2-methoxyphen-1-yl.

In a further embodiment, $R^2$ represents an optionally substituted pyridyl, such as fluoropyridyl, in particular 2-fluoropyridin-5-yl.

In a special embodiment the chemical compound of the invention is
5-[1-(3-Bromo-phenyl)-1H-imidazol-4-yl]-3-methyl-[1,2,4]oxadiazole;
5-(1-Biphenyl-3-yl-1H-imidazol-4-yl)-3-methyl-[1,2,4]oxadiazole;
5-[1-(2',5'-Dimethoxy-biphenyl-3-yl)-1H-imidazol-4-yl]-3-methyl-[1,2,4]oxadiazole;
5-[1-(2'-Methoxy-biphenyl-3-yl)-1H-imidazol-4-yl]-3-methyl-[1,2,4]oxadiazole;
5-[1-(5'-Fluoro-2'-methoxy-biphenyl-3-yl)-1H-imidazol-4-yl]-3-methyl-[1,2,4]oxadiazole;
5-[1-(2'-Ethyl-biphenyl-3-yl)-1H-imidazol-4-yl]-3-methyl-[1,2,4]oxadiazole;
5-[1-(2'-Ethoxy-biphenyl-3-yl)-1H-imidazol-4-yl]-3-methyl-[1,2,4]oxadiazole;
3-Methyl-5-[1-(2'-trifluoromethoxy-biphenyl-3-yl)-1H-imidazol-4-yl]-[1,2,4]oxadiazole;
3-Methyl-5-[1-(2'-acetyl-biphenyl-3-yl)-1H-imidazol-4-yl]-[1,2,4]oxadiazole;
3-Methyl-5-[1-(2'-fluoro-biphenyl-3-yl)-1H-imidazol-4-yl]-[1,2,4]oxadiazole;
2-Fluoro-5-{3-[4-(3-methyl-[1,2,4]oxadiazol-5-yl)-imidazol-1-yl]-phenyl}-pyridine;
3-Methyl-5-[1-(2'-cyano-biphenyl-3-yl)-1H-imidazol-4-yl]-[1,2,4]oxadiazole;
3-Methyl-5-[1-(2'-carboxylic acid-biphenyl-3-yl)-1H-imidazol-4-yl]-[1,2,4]oxadiazole;
2-[1-(3-Bromo-phenyl)-1H-imidazol-4-yl]-5-methyl-[1,3,4]oxadiazole;
2-[1-(3-Bromo-phenyl)-1H-imidazol-4-yl]-1H-benzoimidazole;
2-[1-(3-Bromo-phenyl)-1H-imidazol-4-yl]-benzooxazole;
2-[1-(3-Bromo-phenyl)-1H-imidazol-4-yl]-benzothiazole;
2-[1-(3-Bromo-phenyl)-1H-imidazol-4-yl]-4,5-dihydro-oxazole;
(R)-2-[1-(3-Bromo-phenyl)-1H-imidazol-4-yl]-5-methyl-4,5-dihydro-oxazole;
N-{3-[4-(5-Methyl-furan-2-yl)-imidazol-1-yl]-phenyl}-acetamide;
1-(1-Biphenyl-3-yl-1H-imidazol-4-yl)-1H-pyrazole;
1'-Biphenyl-3-yl-1'H-[1,4']biimidazolyl;

any of its isomers or any mixture of its isomers, or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

In the context of this invention an aryl group designates a carbocyclic aromatic ring system such as phenyl, naphthyl (1-naphthyl or 2-naphthyl) or fluorenyl.

In the context of this invention a heterocyclic group designates a mono- or bicyclic heterocyclic group, which holds one or more heteroatoms in its ring structure. Preferred heteroatoms include nitrogen (N), oxygen (O), and sulphur (S). The ring structure may in particular be aromatic (i.e. a heteroaryl), saturated or partially saturated.

Examples of preferred saturated or partially saturated heterocyclic monocyclic 5-membered groups of the invention include 1,3-dioxolan, imidazolidine, oxazoline, oxazolidine, oxadiazoline, pyrroline, pyrrolidine, pyrazolidine, and pyrazoline.

Examples of preferred saturated or partially saturated heterocyclic monocyclic 6-membered groups of the invention include 1,4-dioxolane, 1,4-dithiane, morpholine, 1,4-oxazine, oxadiazine, piperidine, piperazine, dihydro-pyrane, tetrahydro-pyrane, thiomorpholine, 1,3,5-trithiane.

Examples of preferred saturated or partially saturated heterocyclic monocyclic 7-membered groups of the invention include homopiperidine and homopiperazine.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, tetrazolyl, 1,2,4-oxadiazolyl, 1,2,5-oxadiazolyl, 1,3,4-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, pyridazinyl or pyrazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzoxadiazolyl, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus: and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosis regimen may be reduced.

EXAMPLES

The invention is further illustrated with reference to the following examples, which are not intended to be in any way limiting to the scope of the invention as claimed.

Synthesis of Common Intermediates

The synthesis of the intermediates 2 and 3 and the compound 4 is shown in Scheme 1.

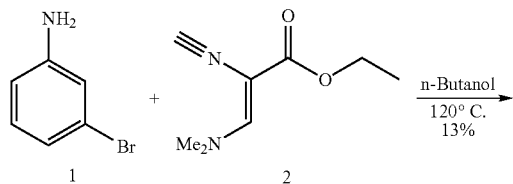

(Scheme 1)

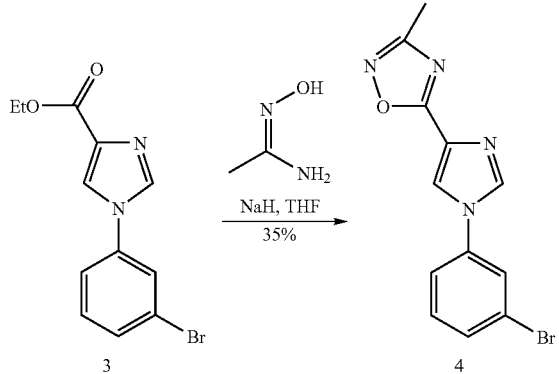

1-(3-Bromo-phenyl)-1H-imidazole-4-carboxylic acid ethyl ester (3)

A solution of compound 1 (11.8 g, 79 mmol) and 3-bromo aniline (2) (11.3 g, 65 mmol) in n-butanol (90 mL) was heated to reflux for 72 h [reaction was monitored by TLC]. Reaction mixture was concentrated under reduced pressure to remove n-butanol and the residue was passed through silica gel column, eluated with mixture of ethyl acetate and hexane to give mixture of ethyl and n-butyl ester compounds which was then separated by flash column chromatography over silica gel using 3:7 mixture ethylacetate and hexane as eluant. Finally ethyl ester was further purified by crystallization to furnish 3 (2.5 g, 13%) as brown solid.

5-[1-(3-Bromo-phenyl)-1H-imidazol-4-yl]-3-methyl-[1,2,4]oxadiazole (4)

To a suspension of NaH (1.30 g, 32.64 mmol, 60% in mineral oil) in THF (15 mL) under nitrogen atmosphere was added N-hydroxy-acetamidine (2.62 g, 35.4 mmol) and stirred for 1 h at room temperature. The bromo ester 3 (8 g, 27.2 mmol) in THF (2 mL) was added and refluxed for 12 h. The reaction mixture was quenched by adding brine, extracted with ethylacetate (100 mL) and dried over anhydrous $Na_2SO_4$. The organic layer was concentrated under reduced pressure and purified by flash chromatography using 25% ethylacetate in hexane as mobile phase to furnish 4 (2.8 g, 35%) as pale yellow solid, mp=200.1-202.4° C.

General Procedure for Suzuki Coupling Products of 4

Method A

To a solution of aryl bromide 4 (1 eq.) in mixture of solvents 1,2-dimethoxyethane and water (2:1) was added arylboronic acid (2 eq) and sodium carbonate (1.5 eq) and degasified by bubbling nitrogen for a period of 30 min. The catalyst $(Ph_3P)_2PdCl_2$ (10 mol %) was added and heated at 90° C. for 4-12 h. (The reaction was monitored by TLC). The crude mixture was filtered through celite bed, washed with ethylacetate, dried over $Na_2SO_4$. The combined organic layer was concentrated and purified by silica gel column chromatography using 20-25% ethylacetate in hexane to give biaryl compounds in 16-51% yield.

5-(1-Biphenyl-3-yl-1H-imidazol-4-yl)-3-methyl-[1,2,4]oxadiazole

The general procedure, 4, and benzene boronic acid was used to give the title compound (250 mg, 51%) as a white solid, mp=162.9-165.2° C.

5-[1-(2',5'-Dimethoxy-biphenyl-3-yl)-1H-imidazol-4-yl]-3-methyl-[1,2,4]oxadiazole The general procedure, 4, and 2,5-dimethoxyphenylboronic acid was used to give the title compound (120 mg, 33%) as a white solid, mp=126.9-128.8° C.

5-[1-(2'-Methoxy-biphenyl-3-yl)-1H-imidazol-4-yl]-3-methyl-[1,2,4]oxadiazole The general procedure, 4, and 2-methoxyphenylboronic acid was used to give the title compound (130 mg, 40%) as a white solid, mp=97.1-100.7° C.

5-[1-(5'-Fluoro-2'-methoxy-biphenyl-3-yl)-1H-imidazol-4-yl]-3-methyl-[1,2,4]oxadiazole The general procedure, 4, and 5-fluoro-2-methoxyphenylboronic acid was used to give the title compound (105 mg, 23%) as a white solid, mp=153.1-157.6° C.

5-[1-(2'-Ethyl-biphenyl-3-yl)-1H-imidazol-4-yl]-3-methyl-[1,2,4]oxadiazole

The general procedure, 4, and 2-ethylphenylboronic acid was used to give the title compound (95 mg, 29%) as a white solid, mp=150.4-156.1° C.

5-[1-(2'-Ethoxy-biphenyl-3-yl)-1H-imidazol-4-yl]-3-methyl-[1,2,4]oxadiazole

The general procedure, 4, and 2-ethoxyphenylboronic acid was used to give the title compound (55 mg, 16%) as a white solid, mp=110.2-112.7° C.

3-Methyl-5-[1-(2'-trifluoromethoxy-biphenyl-3-yl)-1H-imidazol-4-yl]-[1,2,4]oxadiazole The general procedure, 4, and 2-(trifluoromethoxy)phenylboronic acid was used to give the title compound (160 mg, 42%) as a white solid, mp=141.6-143.9° C.

3-Methyl-5-[1-(2'-acetyl-biphenyl-3-yl)-1H-imidazol-4-yl]-[1,2,4]oxadiazole

The general procedure, 4, and 2-(acetylphenyl)boronic acid was used to give the title compound (60 mg, 16%) as a white solid, mp=143.8-146.2° C.

3-Methyl-5-[1-(2'-fluoro-biphenyl-3-yl)-1H-imidazol-4-yl]-[1,2,4]oxadiazole

The general procedure, 4, and 2-(fluorophenyl)boronic acid was used to give the title compound. HRMS (ESI$^+$): m/z=320.3257 [M+H]

2-Fluoro-5-{3-[4-(3-methyl-[1,2,4]oxadiazol-5-yl)-imidazol-1-yl]-phenyl}-pyridine The general procedure, 4, and 2-fluoropyridine-5-boronic acid was used to give the title compound. HRMS (ESI$^+$): m/z=321.3138 [M+H]

3-Methyl-5-[1-(2'-cyano-biphenyl-3-yl)-1H-imidazol-4-yl]-[1,2,4]oxadiazole

The general procedure, 4, and 2-(cyanophenyl)boronic acid was used to give the title compound in 3% yield. HRMS (ESI$^+$): m/z=327.3457 [M+H]. From the same reaction, 3-Methyl-5-[1-(2'-carboxylic acid-biphenyl-3-yl)-1H-imidazol-4-yl]-[1,2,4]oxadiazole was isolated in 3% yield by column chromatography in a pure form. HRMS (ESI$^+$): m/z=324.3814 [M+H]

Synthesis of Common Intermediates

The synthesis of the intermediates 5, and 6 and the compound 7 is shown in Scheme 2.

(Scheme 2)

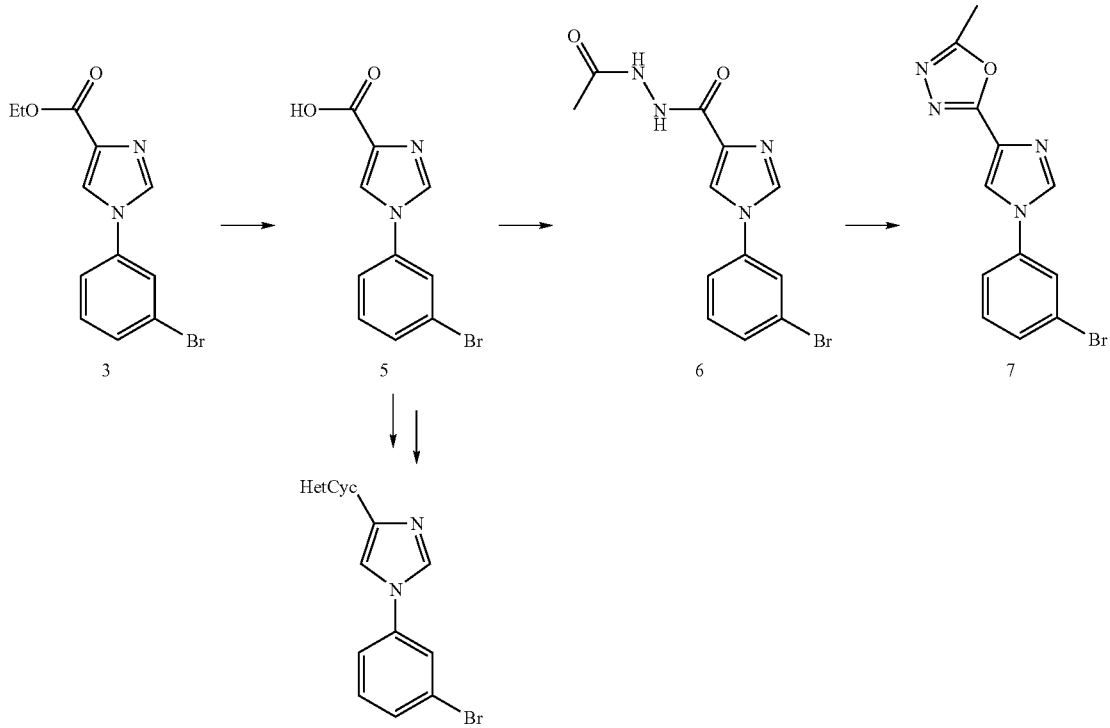

1-(3-Bromo-phenyl)-1H-imidazole-4-carboxylic acid (5)

To a solution of 3 (0.5 g, 1.7 mmol) in methanol (25 mL) was added aqueous NaOH (2M; 4.3 mL) and the reaction mixture was stirred at 40° C. for 0.5 h. Methanol was removed in vacuo and the water layer acidified and extracted with ethyl acetate, dried, filtered and evaporated to dryness. The crude compound was used as such for the next step.

General Amide Formation

Method B

1-(3-Bromo-phenyl)-1H-imidazole-4-carboxylic acid N'-acetyl-hydrazide (6)

To a solution of 5 (0.30 g, 1.1 mmol), acethydrazide (82 mg, 1.1 mmol) diisopropylethyl amine (975 uL, 5.6 mmol), and 1-hydroxy-7-azabenzotriazole (HOAt, 177 mg, 1.3 mmol) in DMF (10 mL) was added and 1-(3-dimethylamino-propyl)-3-ethylcarbodiimide, hydrochloride (EDC HCl; 249 mg, 1.3 mmol). The mixture was stirred at room temperature for 16 h. The solvent was evaporated and the residue was extracted with hot ethyl acetate. The solvent was evaporated and crystallised from MeOH to give the title compound.

2-[1-(3-Bromo-phenyl)-1H-imidazol-4-yl]-5-methyl-[1,3,4]oxadiazole

A suspension of 6 (50 mg, 0.15 mmol) in PPA was heated to 155° C. for 1 h and then allowed to cool to room temperature. the reaction mixture was carefully diluted using 6% $NH_4OH$ aqueous solution to pH=8. The precipitate formed was isolated by filtration to afford 715 mg (33%) as a white solid. HRMS (ESI$^+$): m/z=305.1341 [M+H]

Procedure for Cyclisation

Method C

2-[1-(3-Bromo-phenyl)-1H-imidazol-4-yl]-1H-benzoimidazole 1-(3-Bromo-phenyl)-1H-imidazole-4-carboxylic acid 5 (150 mg, 0.56 mmol) was added to PPA (preheated to 140° C.) and the mixture was stirred until a thick homogeneous solution was obtained. 1,2-Phenyldiamine (67 mg, 0.62 mmol) was added and the mixture was heated for 6 h at 200° C. After cooling to room temperature it was carefully diluted with 6% $NH_4OH$ aqueous solution until the pH=8. The precipitate formed was isolated by filtration, dissolved in little ethyl acetate and filtrated again. Concentration of the organic layer afforded 72 mg (38%) of the title compound as a purple solid. HRMS (ESI$^+$): m/z=339.1949 [M+H]

2-[1-(3-Bromo-phenyl)-1H-imidazol-4-yl]-benzooxazole

The title compound was prepared by Method C by using 2-aminophenol. HRMS (ESI$^+$): m/z=307.3513 [M+H]

2-[1-(3-Bromo-phenyl)-1H-imidazol-4-yl]-benzothiazole

The title compound was prepared by Method C by using 2-aminothiophenol. HRMS (ESI$^+$): m/z=356.246 [M+H]

1-(3-Bromo-phenyl)-1H-imidazole-4-carboxylic acid (2-hydroxy-ethyl)-amide

The title compound was prepared by Method B and ethanolamine.

2-[1-(3-Bromo-phenyl)-1H-imidazol-4-yl]-4,5-dihydro-oxazole 1-(3-Bromo-phenyl)-1H-imidazole-4-carboxylic acid (2-hydroxy-ethyl)-amide (140 mg, 0.45 mmol) was dissolved in $CH_2Cl_2$ under argon atmosphere and triethyl amine (321 μL, 2.3 mmol) and para-toluene sulfonic acid (95 mg; 0.5 mmol) were added. After heating for 20 h at reflux the reaction mixture was diluted with water and refluxed for 45 min. After cooling to room temperature the layers were separated and the organic phase was washed with water and dried over $Na_2SO_4$. Concentration of the organic layer followed by column chromatography on silica gel with a gradient of 1%-5% MeOH in $CH_2Cl_2$ afforded 25 mg (19%) of the title product. HRMS (ESI$^+$): m/z=292.135 [M+H]

1-(3-Bromo-phenyl)-1H-imidazole-4-carboxylic acid (R)-2-hydroxy-propyl)-amide The title compound was prepared by Method B and (R)-2-hydroxypropylamine. HRMS (ESI$^+$): m/z=306.1618 [M+H]

(R)-2-[1-(3-Bromo-phenyl)-1H-imidazol-4-yl]-5-methyl-4,5-dihydro-oxazole

The title compound was prepared from 1-(3-Bromo-phenyl)-1H-imidazole-4-carboxylic acid (R)-2-hydroxy-propyl)-amide by a method similar to that used to synthesise 2-[1-(3-Bromo-phenyl)-1H-imidazol-4-yl]-4,5-dihydro-oxazole.

Synthesis of Common Intermediates

The synthesis of the intermediates 8, 9, 10, 11 and 12 is shown in Scheme 3.

(Scheme 3)

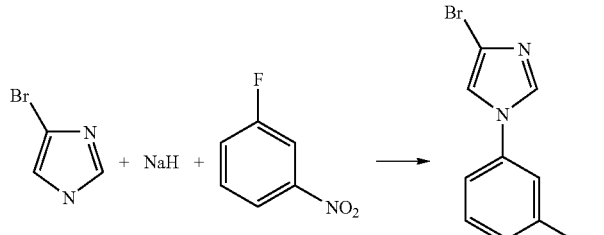

8

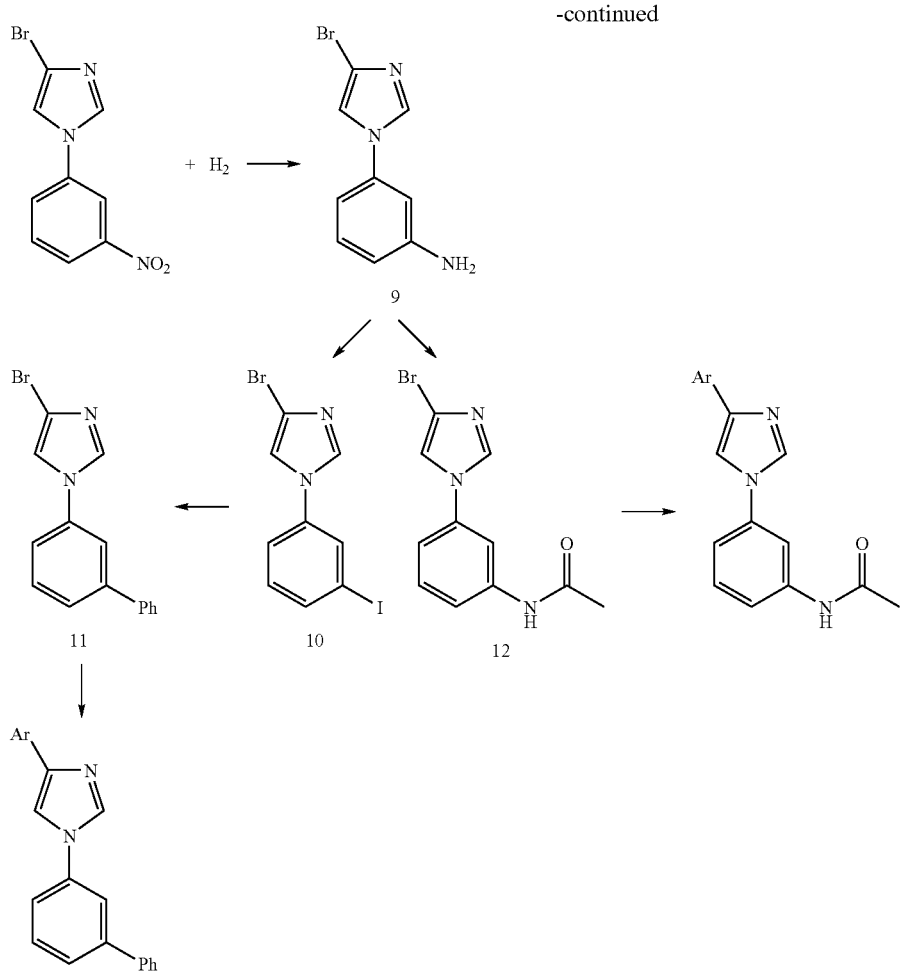

-continued

4-Bromo-1-(3-nitro-phenyl)-1H-imidazole (8)

To a solution of 4-bromo-imidazole (32 g; 217.7 mmol) in DMF (300 mL) was carefully added NaH (60% dispension; 10.8 g; 270 mmol) such that the temperature did not exceed 30° C. The slurry was stirred for 20 min after which 3-nitrofluorobenzene 35 mL; 329 mmol) was added. The reaction mixture was stirred for another 30 min, heated to 150° C. and left with stirring overnight. The reaction mixture was poured onto 750 mL of ice-water under stirring. The precipitate was isolated by filtration, washed with $H_2O$, air-dried and triturated with a diethyl ether-petrol ether (bp=80-100° C.) mixture (100 mL+100 mL) to give after filtration and drying of the solid 70 g crude product.

3-(4-Bromo-imidazol-1-yl)-phenylamine (9)

To a solution of 1 (2.68 g; 10 mmol) was added 99% ethanol (25 mL) and THF (5 mL). The mixture was stirred under a hydrogen atmosphere (1 atm) and heated to approx. 40° C. After consumption of approx. 660 mL of $H_2$ the reaction mixture was filtered through Celite® and evaporated to dryness giving an yellow oil. The crude product was dissolved in EtOAc (30 mL) and extracted twice with 0.4 M HCl (aq, 2×50 mL). The combined aqueous phases were made alkaline using 4 M NaOH (aq) and shaken with $CH_2Cl_2$ (100 mL). The mixture was run through a Phase Separator® and evaporated to dryness giving 1.2 g of a yellow solid. The solid may be further purified by conventional column chromatography to give a pure compound.

4-Bromo-1-(3-iodo-phenyl)-1H-imidazole (10)

A solution of 2 (12.35 g; 52 mmol) in conc. hydro chloric acid (125 mL) was cooled to 0° C. after which an ice-cold solution of $NaNO_2$ (4.0 g; 57 mmol) in $H_2O$ (15 mL) was added at a rate that maintained the temperature <5° C. The mixture was stirred at 0-5° C. for 20 min after which an ice-cold solution of KI (9.1 g; 55 mmol) in $H_2O$ (55 mL) was added and the mixture was allowed to warm to room temperature at which temperature it was stirred for 3 h. The reaction mixture was then heated to 60° C. for 20 min, allowed to cool to room temperature and left with stirring over night. The mixture was neutralised using $K_2CO_3$ (s) while maintaining the temperature below 30° C., extracted with EtOAc and the organic phase dried to give after filtration and evaporation the crude product (13.85 g) as a red-brown semi-solid. The crude product was purified by CombiFlash 16qx (80 g+40 g columns, eluent 100% petrol ether (bp=80-100° C.) to 100% ethyl acetate) to yield 3.7 g (20%) pure product.

1-Biphenyl-3-yl-4-bromo-1H-imidazole (11)

A solution of 3 (3.7 g; 10.6 mmol), benzene boronic acid (1.36 g; 11.1 mmol) and $K_2CO_3$ (5.9 g; 42.4 mmol) in dimethoxy ethane (10 mL) and $H_2O$ (5 mL) was purged with argon and $Cl_2Pd(PPh_3)_2$ (400 mg; 5 mol %) was added. The reaction mixture was heated to reflux over night and added EtOAc and brine. The organic phase was isolated, dried using $MgSO_4$, filtered and evaporated to dryness yielding 3.42 g. The crude product was purified by CombiFlash 16qx (80 g column, eluent 100% petrol ether (bp=80-100° C.) to 100% ethyl acetate) to give 1.53 g (48%) pure product.

N-[3-(4-Bromo-imidazol-1-yl)-phenyl]-acetamide (12)

To a solution of 2 (3 g; 12.6 mmol) in $CH_2Cl_2$ (10 mL) at 0° C. was added diisopropyl ethyl amine (2.19 mL; 12.6 mmol) and acetic anhydride (1.24 mL; 13.2 mmol). The reaction was allowed to warm to room temperature and stirred over night. The reaction mixture was washed with 1 M HCl (aq), dried using $MgSO_4$, filtered, and evaporated to dryness giving a quantitative yield of pure product.

N-{3-[4-(5-Methyl-furan-2-yl)-imidazol-1-yl]-phenyl}-acetamide

A slurry of 12 (140 mg; 0.5 mmol), 5-methylfuran-2-boronic acid (88.1 mg; 0.7 mmol), $Cs_2CO_3$ (179 mg, 0.55 mmol) and propane-1,3-diol (53 mg; 1.4 mmol) in $CH_3CN$ (4 mL) was purged with argon and $Cl_2Pd(PPh_3)_2$ (7 mg; 2 mol %) was added. The mixture was heated in EmrysOptimiser (170° C., 15 min). The reaction mixture was filtered hot through a fritte and the precipitate was extracted with hot $CH_3CN$ (8 mL), which was filtered through the same fritte and pooled with the first fraction. The yellow solution was evaporated to dryness and redissolved in 1 mL $CH_3CN$ which was purified by preparative LC-MS to give pure title compound 16 mg (11%). HRMS (ESI$^+$): m/z=281.3135 [M+H]

1-(1-Biphenyl-3-yl-1H-imidazol-4-yl)-1H-pyrazole

Pyrazole (68.3 mg, 1.0 mmol), $K_2CO_3$ (139 mg, 1.0 mmol), CuI (9.5 mg, 5 mol %) and 11 (150 mg, 0.5 mmol) were added to vial and added NMP (1 mL). The slurry was heated in micro wave (emrys optimiser; fixed hold time) to 180° C. for 1 h after which after it was added NMP (1 mL) and heated to 195° C. for 3 h. The reaction mixture was then added another 6.5 mg CuI and 40 mg pyrazole, and heated for another 4 h after by which LC-MS analysis showed full conversion. The rx was added dropwise to $H_2O$ (10 mL) followed by ethyl acetate (30 mL) and brine (10 mL). The phases were separated and the aqueous phase extracted with THF (2×5 mL). The combined organic phases was washed with $H_2O$ (2×5 mL), dried ($MgSO_4$), decanted and evaporated onto Celite and purified by CombiFlash sq16 to yield 47 mg (32%) the title compound as a white solid. HRMS (ESI$^+$): m/z=286.3366 [M+H]

1'-Biphenyl-3-yl-1'H-[1,4']biimidazolyl

The title compound was prepared by a method analogous to the synthesis of 1-(1-Biphenyl-3-yl-1H-imidazol-4-yl)-1H-pyrazole and using imidazole to give 60% yield. HRMS (ESI$^+$): m/z=286.3366 [M+H]

Test Methods

In Vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = (\text{applied test substance concentration, µM}) \times \frac{1}{\left(\frac{C_o}{C_x} - 1\right)}.$$

where $C_o$ is specific binding in control assays, and $C_x$ is the specific binding in the test assay.

(The calculations assume normal mass-action kinetics).

Test results from these experiments with a number of compounds of the invention are shown in Table 1 below.

TABLE 1

| Test compound | In vitro binding $IC_{50}$ (µM) |
|---|---|
| 3-Methyl-5-[1-(2'-trifluoromethoxy-biphenyl-3-yl)-1H-imidazol-4-yl]-[1,2,4]oxadiazole | 0.017 |
| 3-Methyl-5-[1-(2'-fluoro-biphenyl-3-yl)-1H-imidazol-4-yl]-[1,2,4]oxadiazole | 0.033 |
| 2-Fluoro-5-{3-[4-(3-methyl-[1,2,4]oxadiazol-5-yl)-imidazol-1-yl]-phenyl}-pyridine | 0.06 |

The invention claimed is:
1. A compound of the general formula (I):

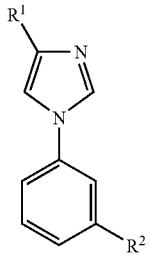

any of its stereoisomers or any mixture of its stereoisomers, or a pharmaceutically acceptable salt thereof,
wherein
$R^1$ represents an oxadiazolyl;
which oxadiazolyl is optionally substituted with one or more substituents independently selected from the group consisting of:
halo, hydroxy, hydroxyalkyl, $R^aR^bN-$, $R^aR^bN$-alkyl, cyano, nitro, trifluoromethyl, trifluoromethoxy, alkoxy, cycloalkoxy, alkyl, cycloalkyl, cycloalkylalkyl, alkenyl, and alkynyl;
wherein $R^a$ and $R^b$ independent of each other are hydrogen or alkyl;
$R^2$ represents
an aryl or heteroaryl group;
which aryl or heteroaryl group is optionally substituted with one or more substituents independently selected from the group consisting of:
halo, cyano, nitro, trifluoromethyl, trifluoromethoxy, alkoxy, $R^e-(C=O)-$, $R^e-O-(C=O)-$ and alkyl;
wherein $R^e$ and $R^f$ independent of each other are hydrogen or alkyl.

2. The compound of claim 1, or a pharmaceutically acceptable salt thereof, wherein
$R^1$ represents an oxadiazolyl;
which oxadiazolyl is optionally substituted with one or more alkyl.

3. The compound of claim 1, which is selected from the group consisting of
5-(1-Biphenyl-3-yl-1H-imidazol-4-yl)-3-methyl-[1,2,4]oxadiazole;
5-[1-(2',5'-Dimethoxy-biphenyl-3-yl)-1H-imidazol-4-yl]-3-methyl-[1,2,4]oxadiazole;
5-[1-(2'-Methoxy-biphenyl-3-yl)-1H-imidazol-4-yl]-3-methyl-[1,2,4]oxadiazole;
5-[1-(5'-Fluoro-2'-methoxy-biphenyl-3-yl)-1H-imidazol-4-yl]-3-methyl-[1,2,4]oxadiazole;
5-[1-(2'-Ethyl-biphenyl-3-yl)-1H-imidazol-4-yl]-3-methyl-[1,2,4]oxadiazole;
5-[1-(2'-Ethoxy-biphenyl-3-yl)-1H-imidazol-4-yl]-3-methyl-[1,2,4]oxadiazole;
3-Methyl-5-[1-(2'-trifluoromethoxy-biphenyl-3-yl)-1H-imidazol-4-yl]-[1,2,4]oxadiazole;
3-Methyl-5-[1-(2'-acetyl-biphenyl-3-yl)-1H-imidazol-4-yl]-[1,2,4]oxadiazole;
3-Methyl-5-[1-(2'-fluoro-biphenyl-3-yl)-1H-imidazol-4-yl]-[1,2,4]oxadiazole;
2-Fluoro-5-{3-[4-(3-methyl-[1,2,4]oxadiazol-5-yl)-imidazol-1-yl]-phenyl}-pyridine;
3-Methyl-5-[1-(2'-cyano-biphenyl-3-yl)-1H-imidazol-4-yl]-[1,2,4]oxadiazole; and
3-Methyl-5-[1-(2'-carboxylic acid-biphenyl-3-yl)-1H-imidazol-4-yl]-[1,2,4]oxadiazole;
or any of its stereoisomers or any mixture of its stereoisomers,
or a pharmaceutically acceptable salt thereof.

4. A pharmaceutical composition, comprising a therapeutically effective amount of a compound of claim 1, any of its stereoisomers or any mixture of its stereoisomers, or a pharmaceutically acceptable salt thereof, together with at least one pharmaceutically acceptable carrier, excipient or diluent.

* * * * *